United States Patent [19]
Roberts et al.

[11] Patent Number: 5,928,163
[45] Date of Patent: Jul. 27, 1999

[54] BIOPSY SAMPLER

[75] Inventors: Troy W. Roberts, Arlington; Bruce H. Diamond, Brookline, both of Mass.

[73] Assignee: Boston Scientific Corporation, Natick, Mass.

[21] Appl. No.: 08/884,043

[22] Filed: Jun. 27, 1997

Related U.S. Application Data

[63] Continuation of application No. 08/414,585, Mar. 31, 1995, abandoned.

[51] Int. Cl.⁶ ............................................. A61B 10/00
[52] U.S. Cl. .................................. 600/567; 606/27
[58] Field of Search .................. 606/39, 40, 41, 606/42, 46, 47, 48, 50, 205, 170, 27; 600/114, 139, 136, 199, 562, 564, 597

[56] References Cited

U.S. PATENT DOCUMENTS

| | | | |
|---|---|---|---|
| 3,892,228 | 7/1975 | MitSui | 600/149 |
| 4,674,499 | 6/1987 | Pao | 606/50 |
| 4,953,559 | 9/1990 | Salerno | 128/751 |
| 5,258,006 | 11/1993 | Rydell et al. | 606/205 |
| 5,352,222 | 10/1994 | Rydell | 606/37 |
| 5,352,234 | 10/1994 | Scott | 606/170 |
| 5,352,235 | 10/1994 | Koros et al. | 606/170 |
| 5,364,395 | 11/1994 | West, Jr. | 606/170 |
| 5,394,885 | 3/1995 | Francese | 128/751 |
| 5,578,030 | 11/1996 | Levin | 606/39 |

*Primary Examiner*—Cary O'Connor
*Assistant Examiner*—Pamela L. Wingood
*Attorney, Agent, or Firm*—Fish & Richardson P.C.

[57] ABSTRACT

The invention features an assembly for taking a biopsy sample from a site within the body of a patient. The assembly includes a resecting device having a cutter near its distal end for resecting and containing a tissue sample and a sheath exterior to the resecting device and sized to be present within the body with the resecting device. The sheath includes an electrode element electrically isolated from the resecting device and disposed on the sheath's outer surface for cauterizing tissue. The resecting device and the sheath cooperate to permit sequential resecting of a tissue sample from a resecting site and cauterizing of the site with the cutter sufficiently spaced from the electrode element to avoid heat damage to the tissue sample.

22 Claims, 8 Drawing Sheets

BIOPSY SAMPLER

This is a continuation of application Ser. No. 08/414,585, filed Mar. 31, 1995, now abandoned.

FIELD OF THE INVENTION

This invention relates to biopsy sampling.

BACKGROUND

There are many biopsy procedures in which tissue samples are taken for later histology. In "cold" biopsy procedures, surgical forceps are inserted within, for example, an endoscope, and are used to resect (i.e., cut) a tissue sample from, for instance, the biliary tree or colon. The forceps, and, hence, the tissue sample, are then removed from the patient through the endoscope.

Extensive bleeding can occur as a result of cold resecting, which can lead to dangerous blood loss levels. Hence, after the tissue sample is removed, another device can be inserted into the patient through the endoscope to stop the bleeding. These devices include tamponade devices which apply pressure to the bleeding site to stop the bleeding, devices which apply alcohol to the bleeding site to stop the bleeding, and electro-cautery devices which apply radio frequency (RF) energy to one or more electrodes (monopolar or bipolar) in contact with the bleeding site to cauterize the tissue and stop the bleeding. Following resecting, time is required to remove the forceps and tissue sample and insert a device to stop the bleeding. During this time, the resecting site continues to bleed.

Alternatively, a "hot" biopsy procedure is performed using surgical forceps in which the jaws are electrodes (bipolar or monopolar). After the tissue sample is resected, the forceps are brought in contact with tissue remaining at the resecting site and RF energy is applied to the forceps to cause current to flow (i.e., cauterization) through the resecting site tissue to coagulate the tissue and stop the bleeding. Coagulation of the tissue may also kill cancerous or precancerous tissue at the resecting site. Often, RF energy is applied to the forceps during resecting to help cut the tissue sample as well.

The tissue sample is again removed from the patient through the endoscope for histology. The tissue sample, however, may be inadvertently cauterized when the resecting site is cauterized rendering the tissue sample unusable for histology, e.g., the question of cell malignancy cannot be answered. The forceps may be lined with insulating material to electrically isolate the tissue sample from the forceps. However, heat generated when the resecting site tissue is cauterized may coagulate the tissue sample within the forceps, again, rendering the tissue sample unusable for histology.

SUMMARY

In one aspect, the invention features an assembly for taking a biopsy sample from a site within the body of a patient. The assembly includes a resecting device having a cutter near its distal end for resecting and containing a tissue sample and a sheath exterior to the resecting device and sized to be present within the body with the resecting device. The sheath includes an electrode element electrically isolated from the resecting device and disposed on the sheath's outer surface for cauterizing tissue. The resecting device and the sheath cooperate to permit sequential resecting of a tissue sample from a resecting site and cauterizing of the site with the cutter sufficiently spaced from the electrode element to avoid heat damage to the tissue sample.

Implementations of the invention may include the following features. The sheath may include a lumen sized to slidably receive the resecting device or the sheath and the resecting device may be constructed as a unitary device where the cutter extends distally of the termination of the sheath and the electrode is spaced proximally of the cutter. The cutter may include forceps. The electrode element may be a monopolar electrode or a pair of bipolar electrodes, and, in both cases, the electrodes may be cylindrical. The bipolar electrodes may also be "C" shaped. Additionally, the sheath may be precurved or the sheath may be deflectable through the use of a tension wire having a distal end fixed toward the distal end of the sheath such that pulling on a proximal end of the tension wire causes a distal portion of the sheath to bend. The sheath may include a lumen disposed in its sidewall for receiving an electrical connection to the electrode element, and the same lumen can be used for receiving the tension wire. The assembly can be sized to pass through an endoscope.

In another aspect, the invention features an assembly for taking a biopsy sample from a site within the body of a patient. The assembly includes a resecting device including forceps near its distal end for resecting and containing a tissue sample, and a sheath exterior to the resecting device and sized to be present within the body with the resecting device. The sheath includes a lumen sized to slidably receive the resecting device and an electrode element electrically isolated from the resecting device and disposed on the sheath's outer surface for cauterizing tissue. The resecting device and the sheath are cooperatively constructed to permit sequential resecting of a tissue sample from a resecting site and cauterizing of the site with the forceps spaced from the electrode element sufficiently to avoid heat damage to the sample.

In another aspect, the invention features an assembly for taking a biopsy sample from a site within the body of a patient. The assembly includes a resecting device including forceps near its distal end for resecting and containing a tissue sample, and a sheath exterior to the resecting device and sized to be present within the body with the resecting device. The sheath and the resecting device are constructed as a unitary device and the forceps extend distally of the termination of the sheath. The sheath includes an electrode element electrically isolated from the resecting device, spaced proximally to the forceps, and disposed on the sheath's outer surface for cauterizing tissue. The resecting device and the sheath are cooperatively constructed to permit sequential resecting of a tissue sample from a resecting site and cauterizing of the site with the forceps spaced from the electrode element sufficiently to avoid heat damage to the sample.

In another aspect, the invention features a method for taking a biopsy sample with an assembly from a site within the body of a patient. The assembly includes a resecting device having a cutter near its distal end for resecting and containing a tissue sample and a sheath exterior to the resecting device and sized to be present within the body with the resecting device. The sheath includes an electrode element electrically isolated from the resecting device and disposed on the sheath's outer surface for cauterizing tissue. The resecting device and the sheath cooperate to permit sequential resecting of a tissue sample from a resecting site and cauterizing of the site with the cutter sufficiently spaced from the electrode element to avoid heat damage to the tissue sample. The method further includes resecting a tissue sample from a resecting site with the resecting device and containing the tissue sample with the cutter. Additionally, the electrode element is located at the resecting site with the cutter containing the sample spaced from the electrode element, and the site is cauterized by application of power to the electrode element.

Implementations of the invention may include the following features. The sheath may include a lumen sized to slidably receive the resecting device, and the method may further include inserting the resecting device within the lumen of the sheath, extending the resecting device from a distal end of the sheath to position the resecting device at a resecting site, and withdrawing the resecting device within the lumen a distance away from the distal end of the sheath. The method may include extending the cutter from the sheath to space the cutter from the electrode. The method may also include withdrawing the resecting device completely from the sheath, removing the tissue sample from the resecting device, reinserting the resecting device within the lumen of the sheath, extending the resecting device from the distal end of the sheath to position the resecting device at a new resecting site, resecting a tissue sample from the new resecting site with the resecting device, containing the tissue sample with the cutter, withdrawing the resecting device within the lumen a distance away from the electrode element, positioning electrode element at new resecting site, and cauterizing the new resecting site by application of power to the electrode element. The method may also include inserting an endoscope within the body and inserting the sheath within the endoscope. Moreover, the sheath and the resecting device may be constructed as a unitary device where the cutter extends distally of the termination of the sheath and the electrode is spaced proximally of the cutter, and the method may further include positioning the resecting device and the sheath along a treatment path, positioning the resecting device at a resecting site, resecting a tissue sample from the resecting site with the resecting device, containing the tissue sample with the cutter, positioning the electrodes at the resecting site, and cauterizing the site by application of power to the electrode element.

Embodiments may include one or more of the following advantages: For example, polyps and other aberrant tissue can be resected and the resection site can be cauterized without heat-damaging the sample or removing the sampling device from the patient's body before cauterizing. For example, in embodiments, the resected tissue is slid axially a predetermined short distance away from the cauterizing electrodes so that heat from the electrodes does not affect the sample integrity. The bleeding of the resecting site is quickly electro-cauterized. The resection can be carried out using a cauterizing sheath having electro-cautery electrodes disposed on a distal end of the sheath and having surgical forceps slidably disposed within a lumen in the sheath. The surgical forceps are used to resect the tissue sample and axially remove the sample from the resecting site, while the electro-cautery electrodes are used to cauterize the resecting site to stop bleeding. In other embodiments, the distance between the electrodes and the forceps is fitted at a preselected spacing sufficient to avoid heat damage when the assembly is maneuvered to position the electrodes at the resection site for cauterization. The need for additional tissue removal, additional biopsy procedures, complications from blood loss, time in surgery, and patient trauma may all be reduced. The instrument can be constructed for use with a variety of existing surgical devices and can be easily manufactured.

Additional advantages and features are apparent from the following.

DETAILED DESCRIPTION

FIG. 7b is an end view of the assembly of FIG. 7a.

STRUCTURE

Referring to FIGS. 1a, 1b, 2, and 3, a biopsy assembly 10 includes a cauterizing sheath 12 and a resecting device 14. Sheath 12 includes a working lumen 16 extending from a proximal end 18 to a distal end 20 defined by an inner lumenal wall 17 and sized to receive resecting device 14. The sheath also includes a pair of bipolar electrodes 22a, 22b mounted on an outer sheath surface 13 near distal end 20. Sheath 12 also includes an electrical connector 24, for connection to a radio frequency (RF) generator (not shown), and a lumen 26, extending between outer surface 13 and inner surface 17 of sheath 12 from electrical connector 24 to electrodes 22a, 22b. Two wires 28 are disposed within lumen 26, and each wire 28 electrically connects one of the electrodes 22a and 22b to electrical connector 24. Wires 28 are each coated with a layer of electrical insulation to prevent electrical contact between the wires.

Resecting device 14 is slidably positioned within working lumen 16 and includes a cutter, for example, forceps 30 (e.g., cup-shaped jaws, 30a, 30b), a handle 32, and a jacket 33. Handle 32 includes a positioning ring 35 and a forceps grip 38. Positioning ring 35 is mechanically coupled to forceps 30 through wires 37, and forceps grip 38 is mechanically coupled to forceps 30 through jacket 33. Positioning ring 35 or jacket 33 is pulled (arrow 34, FIG. 2) to axially withdraw forceps 30 within working lumen 16 toward proximal end 18 of sheath 12 and pushed (arrow 36, FIG. 3) to axially extend forceps 30 from working lumen 24 at distal end 20 of sheath 12. Once extended from working lumen 24, forceps grip 38 is pushed (arrow 36) to open (dashed lines 42a, 42b, FIG. 1b, 3) and pulled (arrow 41) to close (solid lines 44a, 44b, FIG. 1b, 2, 3) jaws 30a and 30b of forceps 30. Because electrodes 22a and 22b are disposed on outer sheath surface 13 and wires 28 are positioned within electrical lumen 26, forceps 30 are electrically isolated from electrodes 22a and 22b.

Handle 32 is used to extend forceps 30 from working lumen 16 beyond distal end 20 of sheath 12 and is used to open jaws 30*a* and 30*b* to surround a tissue sample, e.g., a polyp, and close jaws 30*a* and 30*b* to resect and contain the polyp. Handle 32 is then used to withdraw forceps 30 within working lumen 16 to spatially remove forceps 30, and, hence, the tissue sample, from electrodes 22*a*, 22*b* on distal end 20 of sheath 12. Proximal end 18 of sheath 12 is then pushed to locate electrodes 22*a*, 22*b* adjacent tissue remaining at the resecting site and RF energy is applied to electrodes 22*a*, 22*b*, through electrical connector 24 and wires 28, to electro-cauterize the tissue remaining at the resecting site.

In a particular embodiment, sheath 12 is teflon, which has a low coefficient of friction allowing resection assembly 12, including stainless steel forceps 30, stainless steel coil jacket 33, and stainless steel wires 27 to easily slide within working lumen 16 and a relatively high melting point to prevent sheath 12 from melting when tissue adjacent to electrodes 22*a*, 22*b* is heated during cauterization. Sheath 12 has a wall thickness of approximately 0.15 mm and is about 150 cm in length. In one embodiment, the outer diameter of sheath 12 is about 2.6 mm, the diameter of working lumen 16 is approximately 2.3 mm, and the closed diameter of the jaws of forceps 30 is approximately 2.2 mm which provides about 0.1 mm of clearance between forceps 30 and inner sheath surface 17 when the jaws of forceps 30 are closed and withdrawn within working lumen 16. Such an assembly can be passed through a lumen (i.e., lumen 54, FIG. 4*a*) in an endoscope (i.e., endoscope 50, FIG. 4*a*) having a diameter of about 2.7 mm. Electrodes 22*a* and 22*b* are cylindrical electrodes having a width, W1, of approximately 2.0 mm and are separated along outer sheath surface 13 by a distance, d1, of about 4.0 mm. After forceps 30 have resected and are containing a tissue sample, forceps 30 are withdrawn (arrow 34, FIG. 2) within working lumen 16 a distance d2 of approximately 2 inches or more from electrode 22*b* to prevent the tissue sample from being damaged by cauterization or by heat generated during tissue coagulation.

In another embodiment, the outer diameter of shaft 12 is again 2.6 mm and the diameter of working lumen 16 is again approximately 2.3 mm, however, the closed diameter of the jaws of forceps 30 is approximately 1.8 mm. In yet another embodiment, the outer diameter of shaft 12 is about 3.7 mm, the diameter of working lumen 16 is approximately 3.4 mm and the closed diameter of the jaws of forceps 30 is approximately 3.3 mm.

Use

Referring to FIGS. 4*a*–4*f*, the operation of assembly 10 will be described with regard to the removal of a polyp 46 from a patient's colon 48. The patient is prepared by inserting an endoscope 50 to the region of treatment. The physician, with optical lens 52, inspects the region. Through a lumen 54 in endoscope 50, the region is flushed, e.g., with saline. Outside the body, the resecting device is inserted within the sheath such that the forceps are near but do not extend from the distal end of the sheath.

Figure 1A:
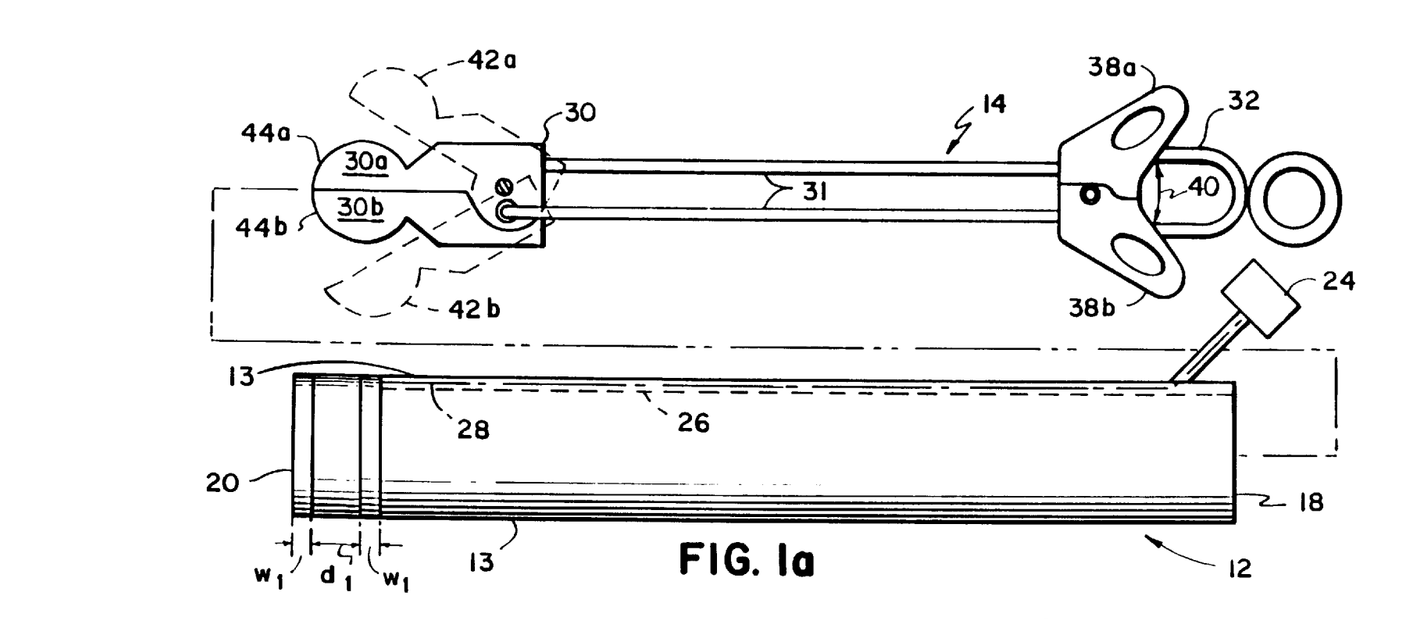
FIG. 1a is an exploded side view of a biopsy assembly including a resecting device and a cauterizing sheath.
Figure 1B:
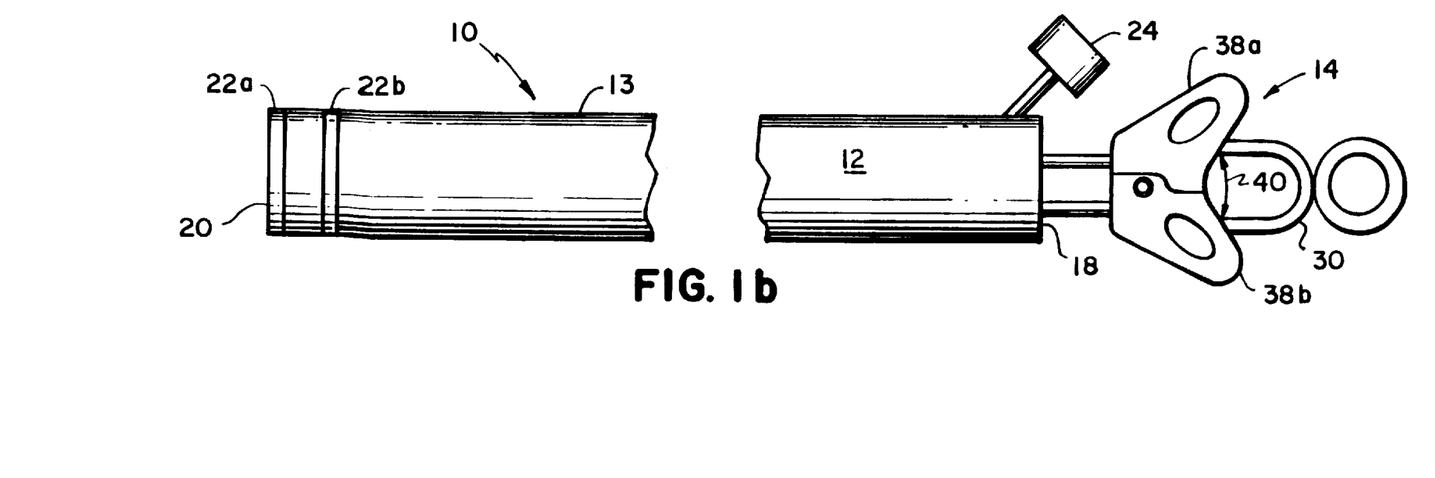
FIG. 1b is view similar to FIG. 1a with the resecting device positioned within the cauterizing sheath.
Figure 2:
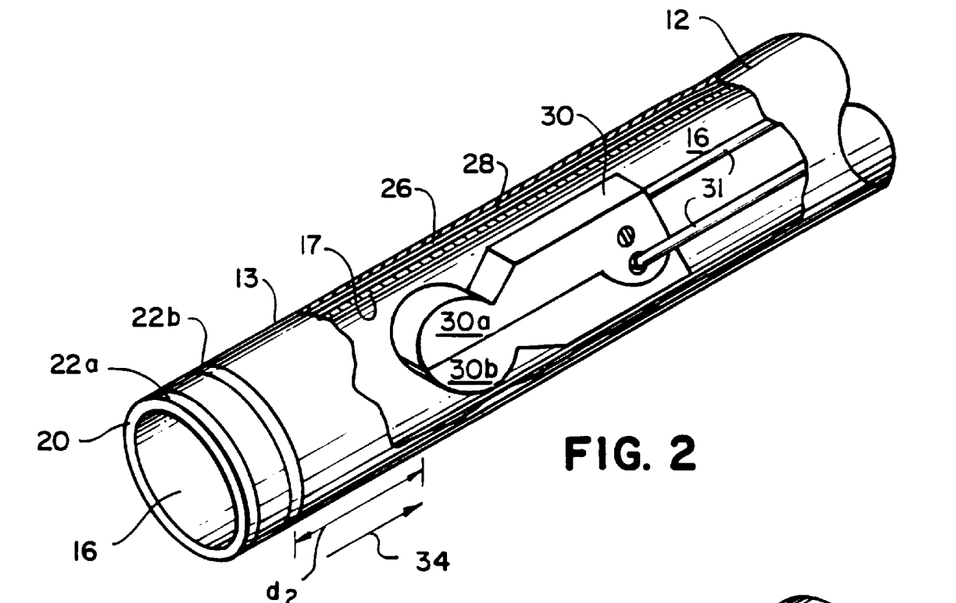
FIG. 2 is an enlarged perspective view of a distal portion of the biopsy assembly of FIG. 1b, with a part of the sheath cut-away.
Figure 3:
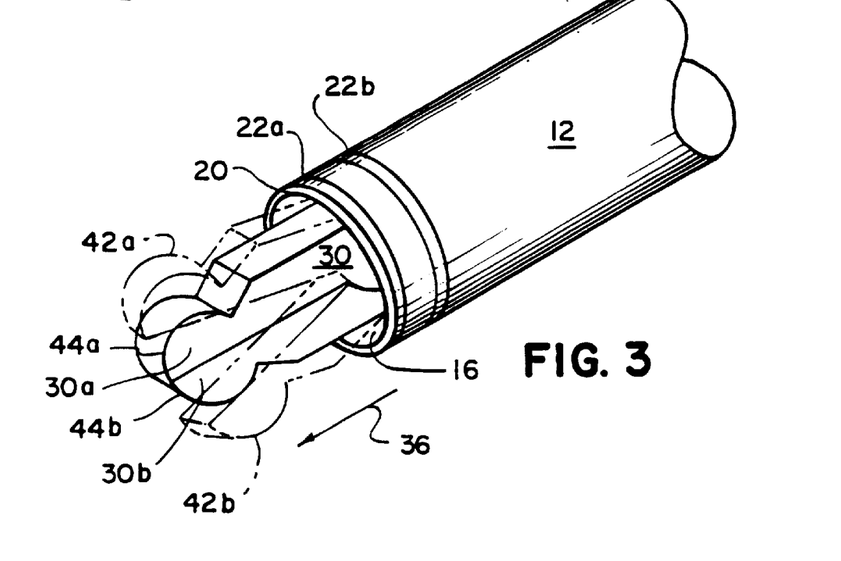
FIG. 3 is an enlarged perspective view of a distal portion of the biopsy assembly of FIG. 1b with surgical forceps of the resecting device axially extended from the cauterizing sheath.
Figure 4A:
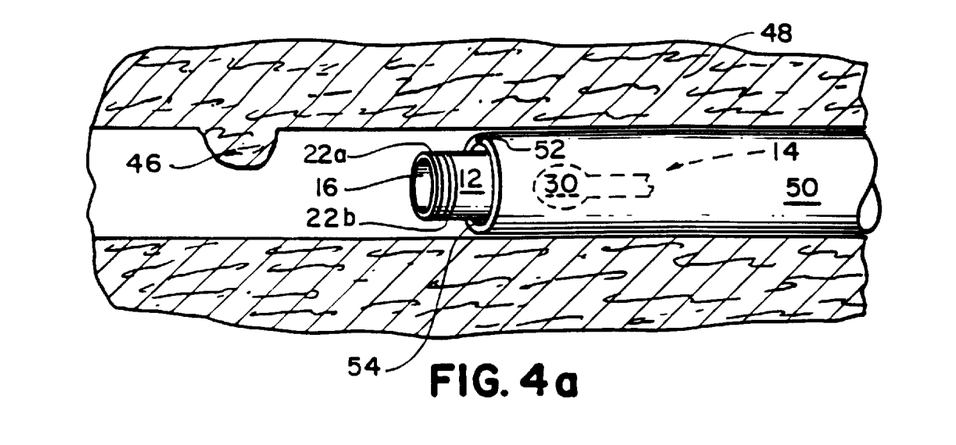
FIGS. 4a–4c and 4f are side views of the distal portion of the biopsy assembly of FIG. 1b disposed within an endoscope and in use within a colon.

Referring particularly to FIG. 4*a*, sheath 12 and resecting device 14 are then inserted together in lumen 54 of endoscope 50. Resecting device 14 provides additional strength to sheath 12 to prevent sheath 12 from buckling as it is inserted within endoscope 50. Alternatively, biopsy assembly 10 can be inserted within endoscope 50 before endoscope 50 is inserted within the patient to save time in surgery.

Figure 4B:
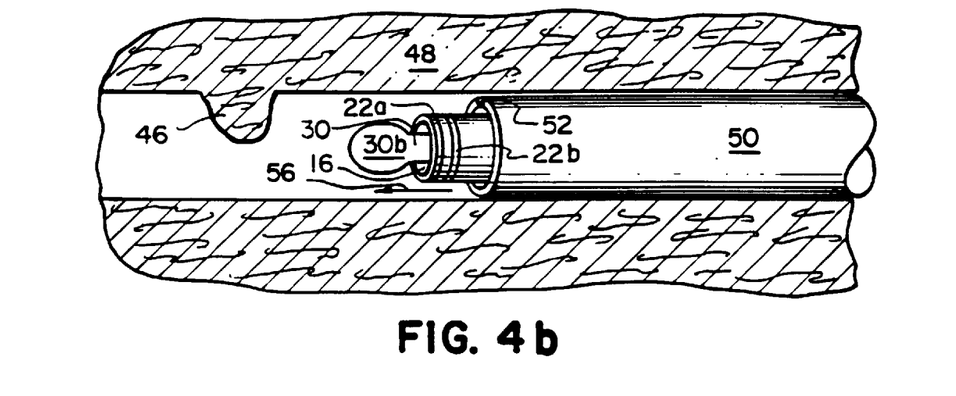
Figure 4C:
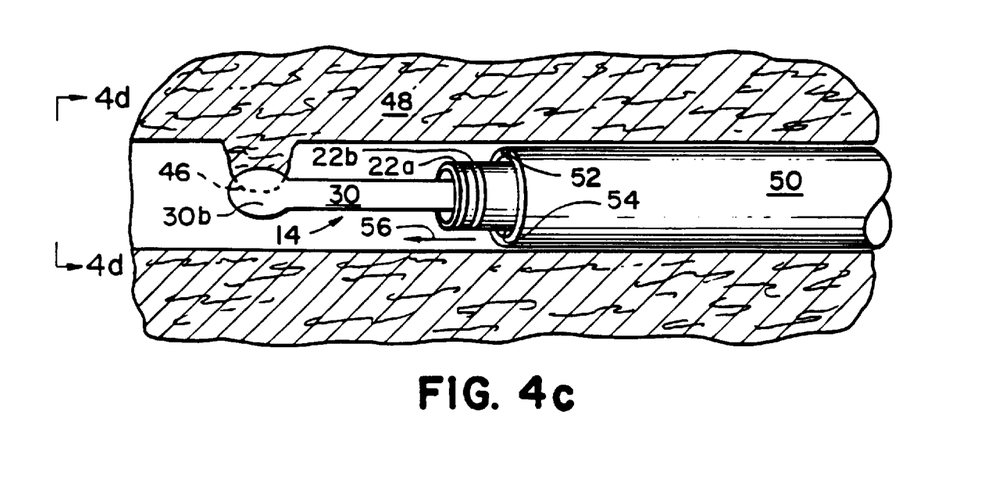
Figure 4D:
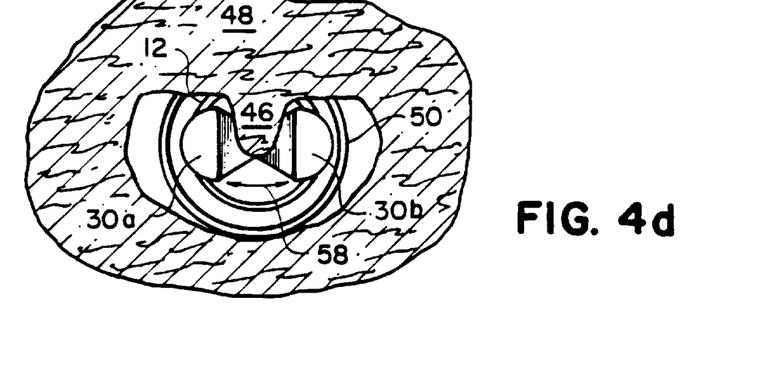
FIGS. 4d and 4e are end views of the distal end of the biopsy assembly of FIG. 1b disposed within an endoscope and in use within a colon.
Figure 4E:
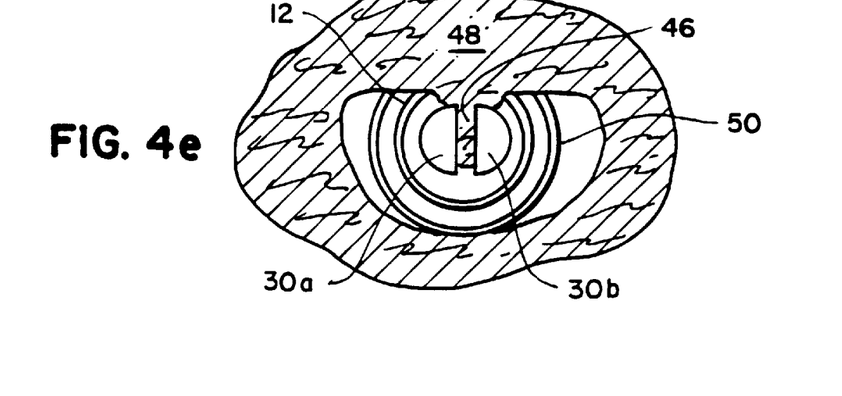

Referring to FIG. 4*b*, once positioned, resecting device 14, including forceps 30, is extended (arrow 56) beyond distal end 20 of sheath 12, and, jaws 30*a*, 30*b* are opened (arrow 58, FIG. 4*c* and 4*d*). As resecting device 14 is further extended, jaws 30*a* and 30*b* surround polyp 46. The jaws are closed (FIG. 4*e*) causing the edges of jaws 30*a* and 30*b* to resect polyp 46 or a portion of polyp 46.

Figure 4F:
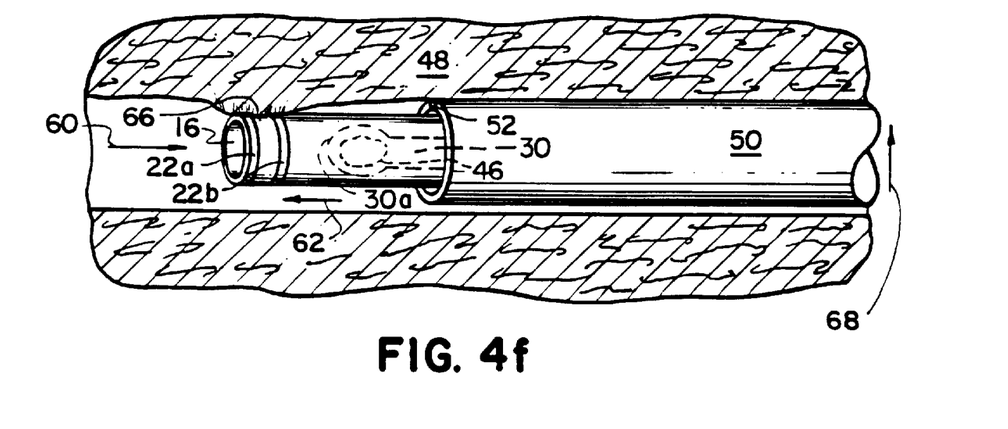

Referring to FIG. 4*f*, resecting device 14, including forceps 30 containing polyp 46, is then withdrawn (arrow 60) within working lumen 16 of sheath 12 approximately 2 inches or more proximal to electrode 22*b*. Sheath 12 is pushed forward (arrow 62) and endoscope 50 is pushed up (arrow 64) to bring electrodes 22*a*, 22*b* in contact with resecting site 66. RF energy is then applied to electrodes 22*a*, 22*b* through wires 28 (FIG. 1*b*) and electrical connector 24 to cause current to pass through the resecting site tissue between electrodes 22*a*, 22*b*. The current heats the resecting site to approximately 60–100° C. which is sufficient to coagulate the resecting site tissue. The distance between forceps 30 and electrodes 22*a*, 22*b* is sufficient to prevent current from traveling through polyp 46 within forceps 30 and sufficient to prevent the heat in the resecting site from coagulating polyp 46 within forceps 30. An irrigant flush, e.g., saline, through working channel 16 can also be used to cool forceps 30 to provide additional protection against coagulation of polyp 46 within forceps 30. As a result, an undamaged tissue sample is taken and the resecting site is quickly cauterized to prevent damaging blood loss.

Endoscope 50, sheath 12, and resecting device 14 may then be removed from the patient and polyp 46 recovered from forceps 30 for histology. Alternatively, only resecting device 14 is removed, through sheath 12 and endoscope 50, from the patient so that polyp 46 can be recovered for histology, and resecting device 14 is then reinserted within sheath 12 and endoscope 50 for removal of another tissue sample.

Other Embodiments

A single cylindrical monopolar electrode can be disposed on the outer sheath surface at the distal end of the sheath. With a monopolar electrode, the patient is placed on a grounding plate, and when RF energy is applied to the electrode, current travels between the electrode and the grounding plate. The current is concentrated in tissue adjacent to the electrode and causes sufficient heat to coagulate the adjacent tissue.

Figure 5:
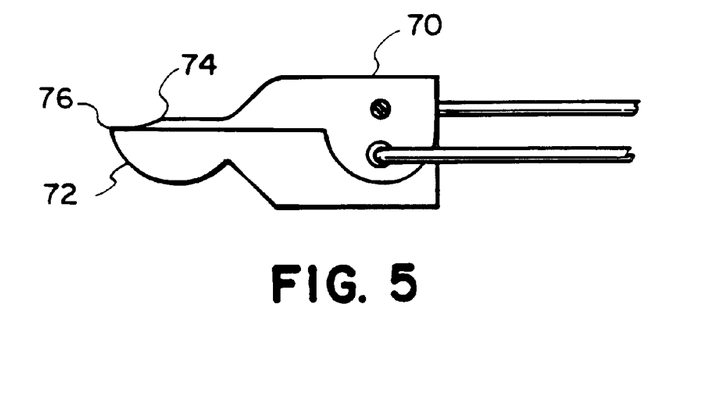
FIG. 5 is a side view of another embodiment of an assembly.

Referring to FIG. 5, forceps 70 can be provided having one cup-shaped jaw 72 and one flat jaw 74, where the flat jaw 74 is sharp along a forward edge 76 and is used to resect tissue that is then caught and contained by cup-shaped jaw 72. Forceps 70 or forceps 30 (FIG. 1*a*) can also include a needle (not shown) to assist in resecting tissue samples.

Figure 6:
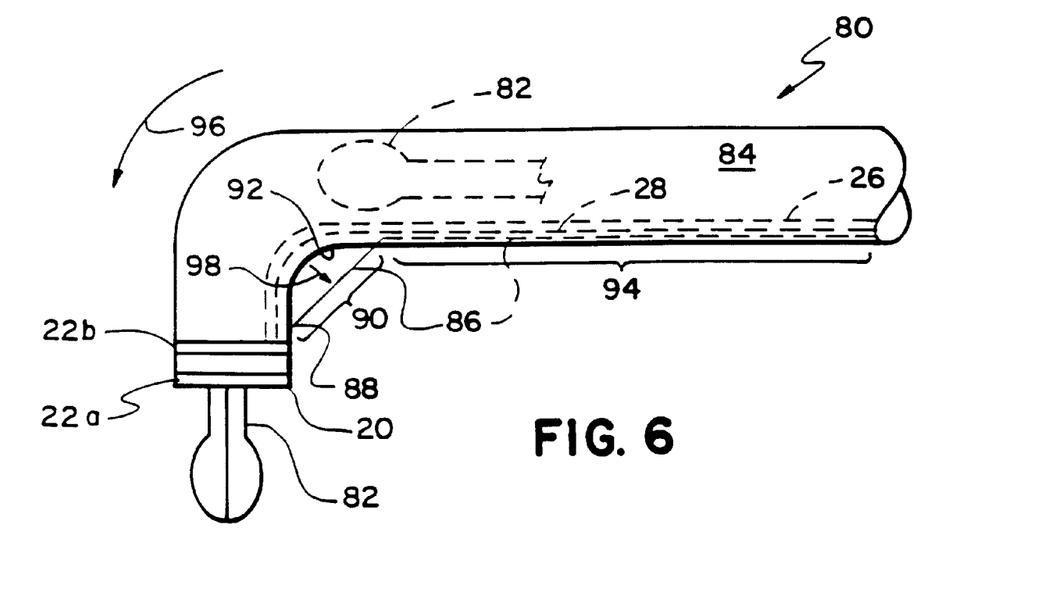
FIGS. 6 and 7a are side views of other embodiments of an assembly.

Referring to FIG. 6, a deflectable sheath 80 includes a resecting assembly 82 slidably disposed within an cauterizing sheath 84. Resecting assembly 82 is similar to resecting assembly 12 described above with respect to FIGS. 1*a* and 1*b*, and sheath 84 is similar to sheath 12 described above, except that sheath 84 includes a tension wire 86 for bending distal end 20 of sheath 84. A distal end 88 of tension wire 86 is fixed to sheath 84. A portion 90 of tension wire 86 extends along an outer surface 92 of sheath 84 and a proximal portion 94 of tension wire 86 extends within electrical lumen 26 of sheath 84. The electrical insulation coating each of the wires 28 prevents electrical contact between tension wire 86 and wires 28.

After positioning sheath 84 and extending resecting assembly 82 beyond a distal end of sheath 84, the physician pulls a proximal end (not shown) of tension wire 86. Because distal end 88 is fixed to sheath 84, pulling on wire 86 causes sheath 84 (and flexible jacket 33, FIG. 1*a*) to bend (arrow 96) and lifts (arrow 98) wire 86 off outer surface 92 of sheath 84. Bending the distal end of sheath 84 allows the physician greater flexibility in removing tissue samples and cauterizing resecting site tissue. Alternatively, sheath 12 (FIGS. 1a, 1b) can be manufactured to be precurved.

Figure 7A:
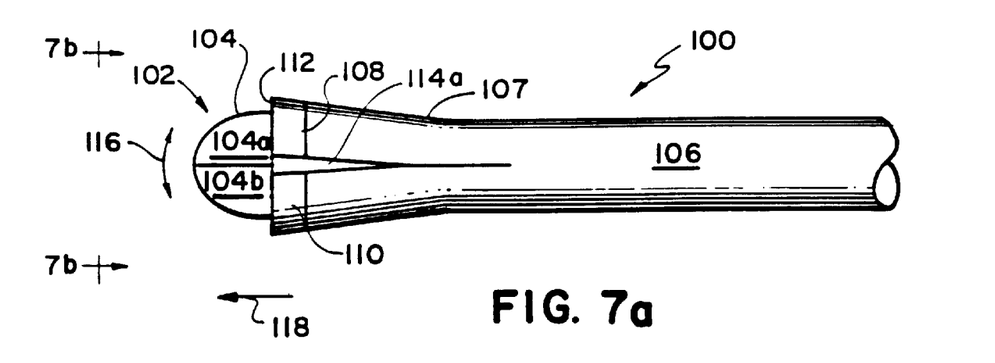
Figure 7B:
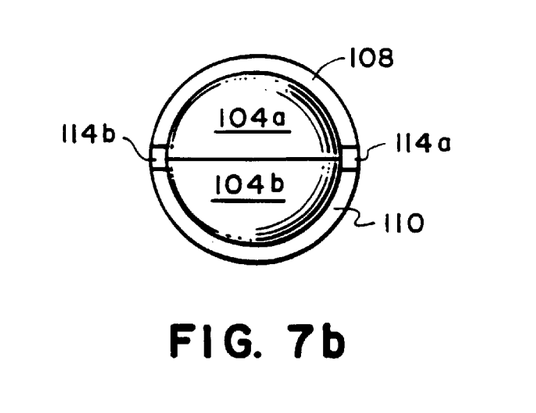

Referring to FIGS. 7a and 7b, a biopsy assembly 100 includes a resecting device 102 including forceps 104 (having jaws 104a and 104b) slidably disposed within cauterizing sheath 106. "C" shaped electrodes 108, 110 are disposed on an outer surface 107 and a distal end 112 of sheath 106 and are separated by elastic members 114a, 114b. The closed diameter of the jaws of forceps 104 is, for example, 3.3 mm, which is larger than the diameter, for example, 3.0 mm, of a lumen (not shown) of sheath 106. Hence, inserting a proximal end of resecting device 102 in distal end 112 of the lumen of sheath 106, eventually pushed forceps 104 against distal end 112 and forces elastic members 114a, 114b to expand (arrow 116).

Biopsy assembly 100 is then inserted within an endoscope and positioned within a patient. Once in position, resecting device 102 is extended (arrow 118) from distal end 112 of sheath 106 and elastic member 114 compresses leaving "C" shaped electrodes 108, 110 separated by a distance of approximately 0.2 mm. Forceps 104 are used to resect a tissue sample from a resecting site, and electrodes 108 and 110 are then brought in contact with the resecting site tissue. Before RF energy is applied to electrodes 108 and 110 to cauterize the resecting site tissue, resecting device 102 is further extended (arrow 118) a predetermined distance (e.g., 2 inches or more) away from distal end 112 of sheath 106. Both sheath 106 and resecting device 102 are then removed together from the endoscope in order to retrieve the tissue sample.

Cylindrical electrodes 22a and 22b (FIG. 1a) can be replaced with two "C" shaped electrodes disposed on distal end 20 of sheath 12 and separated by a fixed distance, e.g., 0.2 mm. With such an arrangement, forceps 30 can be pulled within sheath 12, the distal end of the sheath can be pushed against a resecting site, for example, at a bend or elbow in a colon, and RF energy can be applied to the electrodes to cauterize the resecting site tissue.

Figure 8A:
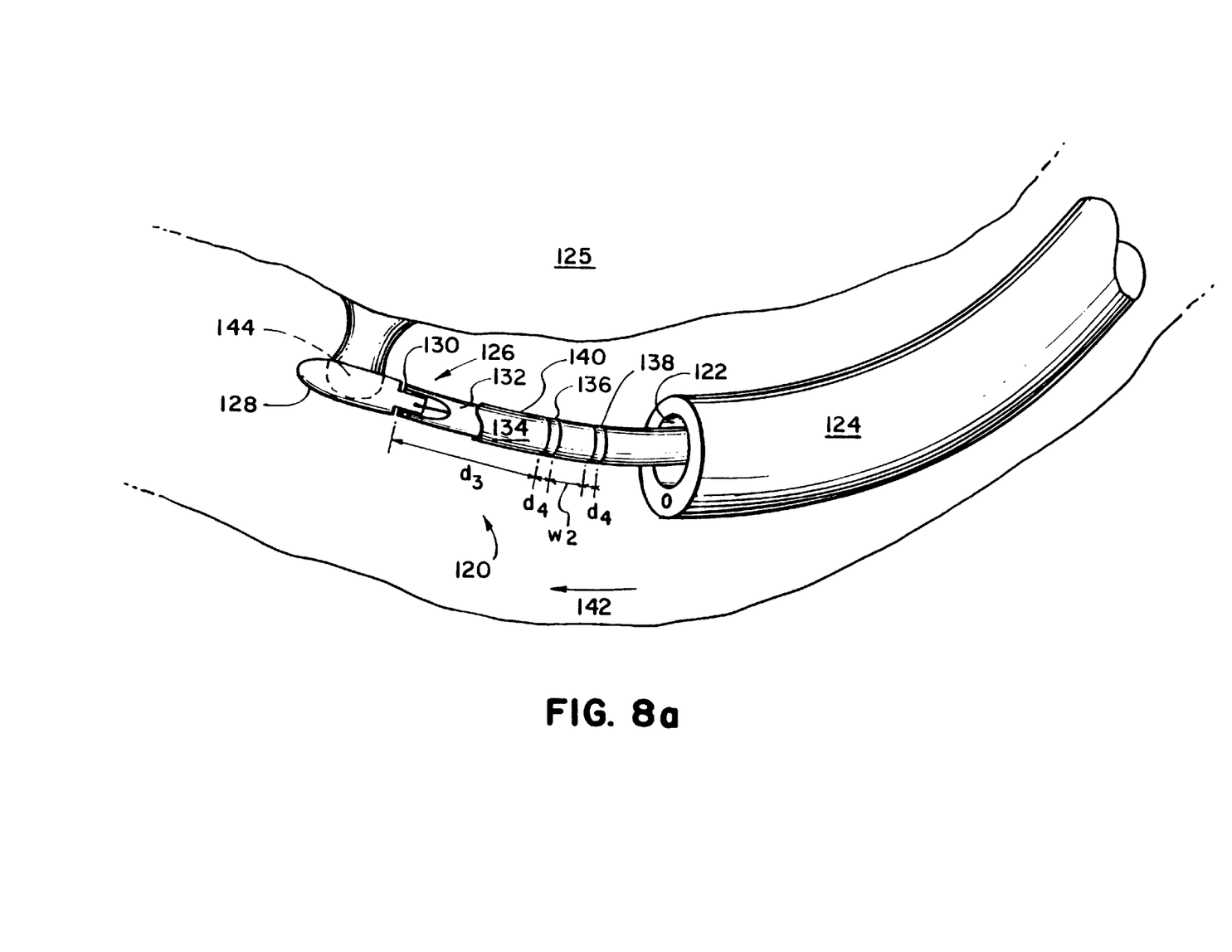
FIGS. 8a and 8b are side views illustrating structure and use of another embodiment of an assembly, with a portion of the assembly of FIG. 8a cut-away.
Figure 8B:
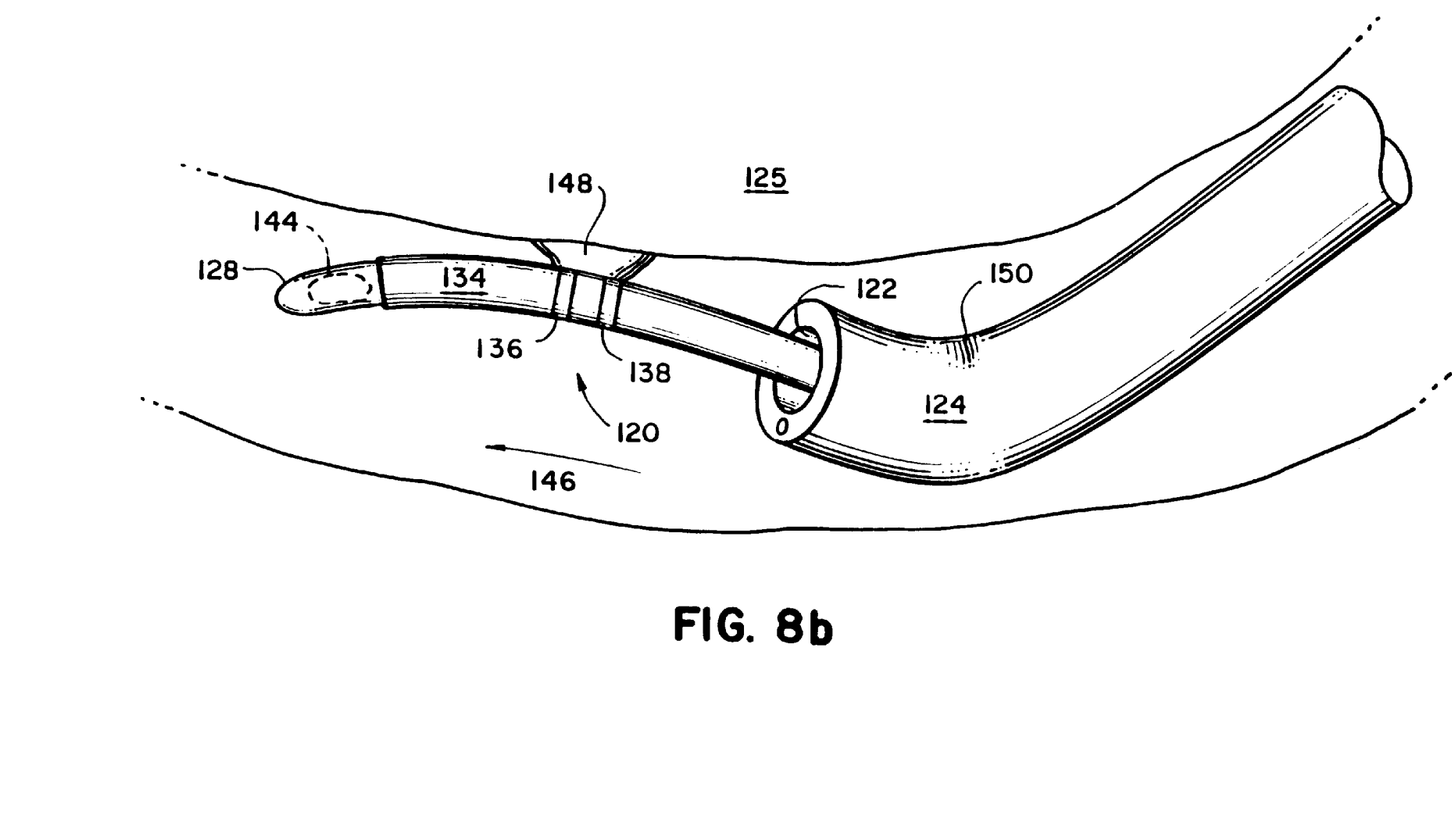

Referring to FIG. 8a and 8b, a biopsy assembly 120 is shown inserted within a lumen 122 of a deflectable endoscope 124 which is positioned within a colon 125 of a patient. Biopsy assembly 120 includes a resecting device 126 having forceps 128 disposed on a distal end 130 of a stainless steel coil 132. A teflon shaft 134 is disposed on stainless steel coil 132, and two cylindrical electrodes 136, 138 are disposed on an outer surface 140 of shaft 134. Shaft 134 electrically isolates forceps 128 from electrodes 136, 138. Shaft 134 is extended (arrow 142, FIG. 8a) through endoscope lumen 122 and the jaws of forceps 128 are opened. Shaft 134 is then further extended to position the opened jaws of forceps 128 around polyp 144. The jaws are then closed to resect polyp 144 and to contain polyp 144. Shaft 134 is then further extended (arrow 146, FIG. 8b) to bring electrodes 136 and 138 toward resecting site 148. Deflectable endoscope 124 is then bent 150 to bring electrodes 136 and 138 in contact with resecting site 148, and RF energy is applied to the electrodes to cauterize tissue at the resecting site 148.

Shaft 134 has a wall thickness of approximately 0.2 mm and is about 150 cm in length. The closed diameter of forceps 128 is about 2.2 mm. The outside diameter of stainless steel coil 132, and, hence, the inside diameter of shaft 134, is also about 2.2 mm. The outside diameter of shaft 134 is about 2.6 mm, and the diameter of endoscope lumen 122 is about 2.7 mm which provides about 0.1 mm of clearance between shaft 34 and the surface of lumen 122. Electrode 136 is separated by a distance, d3, of approximately 2 inches from forceps 128 to prevent tissue samples contained in forceps 128 from being damaged by cauterization or by heat from coagulation. Electrodes 136 and 138 are cylindrical electrodes having a width, W2, of approximately 2.0 mm and are separated by a distance, d4, of about 4.0 mm.

Other embodiments are within the following claims.

What is claimed is:

1. An assembly for taking a biopsy sample from a site within the body of a patient, comprising:

a resecting device including a cutter near its distal end for resecting a tissue sample, and a sheath exterior to said resecting device and sized to be present within the body with said resecting device, said sheath including an electrode element electrically isolated from said cutter and disposed on said sheath's outer surface for cauterizing tissue, and said resecting device and sheath being cooperatively constructed to permit spatial separation between said cutter and said electrode element, said cutter being constructed to hold said tissue sample stationary in a fixed position spaced from said electrode element and to avoid heat damage to said tissue sample held stationary in said fixed position while said electrode element cauterizes said site.

2. The assembly of claim 1 wherein said sheath includes a lumen sized to slidably receive said resecting device.

3. The assembly of claim 1 wherein said sheath and resecting device are constructed as a unitary device wherein said cutter extends distally of the termination of said sheath and said electrode is spaced proximally of said cutter.

4. The assembly of claim 1 wherein said cutter includes forceps.

5. The assembly of claim 1 wherein said electrode element is a monopolar electrode.

6. The assembly of claim 5 wherein said electrode element is a cylindrical electrode.

7. The assembly of claim 1 wherein said electrode element is a pair of bipolar electrodes.

8. The assembly of claim 7 wherein both of said electrodes are cylindrical electrodes.

9. The assembly of claim 7 wherein both of said electrodes are "C" shaped electrodes.

10. The assembly of claim 1 wherein said sheath further includes
a lumen disposed in its sidewall for receiving an electrical connection to said electrode element.

11. The assembly of claim 1 wherein said sheath is precurved.

12. The assembly of claim 1 wherein said sheath is a deflectable sheath including a tension wire having a distal end fixed toward the distal end of said sheath and wherein pulling on a proximal end of said tension wire causes a distal portion of said sheath to bend.

13. The assembly of claim 12 wherein said sheath includes a lumen disposed in its sidewall for receiving a connection to said electrode element and said tension wire.

14. The assembly of claim 1 sized to pass through an endoscope.

15. An assembly for taking a biopsy sample from a site within the body of a patient, comprising:

a resecting device including forceps near its distal end for resecting and containing a tissue sample, and a sheath exterior to said resecting device and sized to be present within the body with said resecting device and including a lumen sized to slidably receive said resecting device, said sheath including an electrode element electrically isolated from said resecting device and disposed on said sheath's outer surface for cauterizing tissue, and said resecting device and sheath being cooperatively constructed to permit sequential resecting of a tissue sample from a resecting site and cauterizing of said site with said forceps spaced from said electrode element in a fixed position and to avoid heat damage to said tissue sample while said site is cauterized and said forceps holds said tissue sample stationary in said fixed position.

16. An assembly for taking a biopsy sample from a site within the body of a patient, comprising:

a resecting device including forceps near its distal end for resecting and containing a tissue sample, and a sheath exterior to said resecting device and sized to be present within the body with said resecting device, wherein said sheath and resecting device are constructed as a unitary device and wherein said forceps extend distally of the termination of said sheath, said sheath including an electrode element electrically isolated from said resecting device, spaced proximally to said forceps, and disposed on said sheath's outer surface for cauterizing tissue, and said resecting device and sheath cooperatively constructed to permit sequential resecting of a tissue sample from a resecting site and cauterizing of said site with said forceps spaced from said electrode element in a fixed position and to avoid heat damage to said tissue sample while said site is cauterized and said forceps holds said tissue sample stationary in said fixed position.

17. A method for taking a biopsy sample from a site within the body of a patient, comprising positioning an assembly as described in claim 1 such that said resecting device and sheath are within the body, resecting a tissue sample from a resecting site with said resecting device and containing said tissue sample with said cutter, locating said electrode element at said resecting site with said cutter containing said sample spaced from said electrode element, and cauterizing said site by application of power to said electrode element.

18. The method of claim 17 wherein said sheath includes a lumen sized to slidably receive said resecting device and wherein said method further comprises the steps of:

inserting said resecting device within said lumen of said sheath, extending said resecting device from a distal end of said sheath and positioning said resecting device at a resecting site, and withdrawing said resecting device within said lumen a distance away from said distal end of said sheath.

19. The method of claim 18, further comprising extending said cutter from said sheath to space said cutter from said electrode.

20. The method of claim 18, further comprising withdrawing said resecting device completely from said sheath, removing said tissue sample from said resecting device reinserting said resecting device within said lumen of said sheath, extending said resecting device from said distal end of said sheath and positioning said resecting device at a new resecting site, resecting a tissue sample from said new resecting site with said resecting device and containing said tissue sample with said cutter, withdrawing said resecting device within said lumen a distance away from said electrode element, positioning said electrode element at said new resecting site, and cauterizing said new resecting site by application of power to said electrode element.

21. The method of claim 17, further comprising, before said positioning step, inserting an endoscope within the body, wherein said sheath is inserted within said endoscope.

22. A method for performing a biopsy procedure, comprising providing an assembly as described in claim 1 wherein said sheath and resecting device are constructed as a unitary device wherein said cutter extends distally of the termination of said sheath and said electrode is spaced proximally of said cutter, positioning said resecting device and said sheath along a treatment path, positioning said resecting device at a resecting site, resecting a tissue sample from said resecting site with said resecting device and containing said tissue sample with said cutter, positioning said electrodes at said resecting site, and cauterizing said site by application of power to said electrode element.

* * * * *